US00PP17438P2

(12) United States Plant Patent
Bergman

(10) Patent No.: US PP17,438 P2
(45) Date of Patent: Feb. 20, 2007

(54) ***CHRYSANTHEMUM* PLANT NAMED 'DAZZLING YONEW YORK'**

(50) Latin Name: *Chrysanthemum×morifolium*
Varietal Denomination: Dazzling Yonew York

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 30 days.

(21) Appl. No.: 11/157,431

(22) Filed: Jun. 21, 2005

(51) Int. Cl.
*A01H 5/00* (2006.01)

(52) U.S. Cl. ..... Plt./287

(58) Field of Classification Search ..... Plt./289, Plt./295, 296, 287
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Dazzling Yonew York', characterized by its uniform and somewhat outwardly spreading plant habit; strong and freely branching growth habit; dark green-colored foliage; uniform flowering response and habit; can be grown as a disbud-type, spray-type or without bud removal; early flowering habit; decorative-type inflorescences with elongated oblong-shaped ray florets; yellow bronze-colored ray florets; and good postproduction longevity with plants maintaining good substance and color for about three weeks in an interior environment.

2 Drawing Sheets

Botanical designation: *Chrysanthemum×morifolium.*
Cultivar denomination: 'Dazzling Yonew York'.

BACKGROUND OF THE INVENTION

The present Invention relates to a new and distinct cultivar of *Chrysanthemum* plant, botanically known as *Chrysanthemum×morifolium* and hereinafter referred to by the name 'Dazzling Yonew York'.

The new *Chrysanthemum* is a product of a planned breeding program conducted by the Inventor in Alva, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* is a naturally-occurring whole plant mutation of the *Chrysanthemum×morifolium* cultivar Yonew York, disclosed in U.S. Plant Pat. No. 15,698. The new *Chrysanthemum* was discovered and selected by the Inventor as a single flowering plant from within a population of plants of the cultivar Yonew York in a controlled environment in Alva, Fla. in April, 2003. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Alva, Fla. in July, 2003. Asexual reproduction by cuttings has shown that the unique features of this new *Chrysanthemum* are stable and reproduced true to type in successive generations.

SUMMARY OF THE INVENTION

The cultivar Dazzling Yonew York has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Dazzling Yonew York'. These characteristics in combination distinguish 'Dazzling Yonew York' as a new and distinct *Chrysanthemum:*

1. Uniform and somewhat outwardly spreading plant habit.
2. Strong and freely branching growth habit.
3. Dark green-colored foliage.
4. Uniform flowering response and habit.
5. Can be grown as a disbud-type, spray-type or without bud removal.
6. Early flowering, eight week response time.
7. Decorative-type inflorescences with elongated oblong-shaped ray florets.
8. Yellow bronze-colored ray florets.
9. Good postproduction longevity with plants maintaining good substance and color for about three weeks in an interior environment.

Plants of the new *Chrysanthemum* can be compared to plants of the parent, the cultivar Yonew York. Plants of the new *Chrysanthemum* differ from plants of the cultivar Yonew York primarily in ray floret coloration as plants of the cultivar Yonew York have light pink-colored ray florets.

Plants of the new *Chrysanthemum* can be compared to plants of the cultivar Yocovington, disclosed in U.S. Plant Pat. No. 13,031. In side-by-side comparisons conducted in Alva, Fla., plants of the new *Chrysanthemum* differed from plants of the cultivar Yocovington in the following characteristics:

1. Plants of the new *Chrysanthemum* were more vigorous than plants of the cultivar Yocovington.

2. Plants of the new *Chrysanthemum* were more outwardly spreading than and not as upright as plants of the cultivar Yocovington.
3. Plants of the new *Chrysanthemum* and the cultivar Yocovington differed in ray floret coloration as plants of the cultivar Yocovington had yellow-colored ray florets.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Dazzling Yonew York' grown as spray-types.

The photograph on the second sheet comprises a close-up view of typical inflorescences of 'Dazzling Yonew York' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Dazzling Yonew York.

Commercial classification: Decorative-type potted *Chrysanthemum.*

Parentage: Naturally-occurring whole plant mutation of the *Chrysanthemum×morifolium* cultivar Yonew York, disclosed in U.S. Plant Pat. No. 15,698.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous decorative-type potted *Chrysanthemum* that can be grown as a disbud-type, spray-type or without bud removal. Upright with lateral branches somewhat outwardly spreading; uniformly mounded crown. Strong and freely branching growth habit; about three to four lateral branches develop after removal of terminal apex (pinching); dense and full plants.

*Plant height.*—About 21 cm.

*Plant width.*—About 34 cm.

*Lateral branches.*—Length: About 15 cm. Diameter: About 4 mm. Internode length: About 2.75 cm. Strength: Strong. Texture: Pubescent. Color: 146A.

*Foliage description.*—Arrangement: Alternate; simple. Length: About 5.6 cm. Width: About 5.1 cm. Apex: Mucronate. Base: Attenuate. Margin: Palmately lobed, sinuses between lateral lobes mostly divergent. Texture, upper and lower surfaces: Pubescent. Color: Developing and fully expanded foliage, upper surface: Darker green than 147A. Developing and fully expanded foliage, lower surface: Close to 147B. Venation, upper surface: Close to 147A. Venation, lower surface: Close to 147B. Petiole length: About 1.8 cm. Petiole diameter: About 3 mm. Petiole texture, upper and lower surfaces: Pubescent. Petiole color, upper surface: Close to 147A. Petiole color, lower surface: Close to 147B.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to two weeks of long day/short night conditions followed by photoinductive short day/long night conditions flower about eight weeks later.

*Postproduction longevity.*—Inflorescences maintain good color and substance for about three weeks in an interior environment.

*Quantity of inflorescences.*—Grown as a spray-type, about five inflorescences develop per lateral branch.

*Inflorescence bud.*—Height: About 5 mm. Diameter: About 7 mm. Shape: Oblate. Color: Close to 146A to 147A.

*Inflorescence diameter.*—About 5.2 cm.

*Inflorescence height.*—About 2.5 cm.

*Diameter of disc.*—About 5 mm; inconspicuous.

*Receptacle diameter.*—About 5 mm.

*Receptacle height.*—About 6 mm.

*Ray florets.*—Length: About 2.7 cm. Width: About 1 cm. Corolla tube length: About 4 mm. Shape: Elongated oblong. Apex: Rounded, acute or emarginate. Base: Fused into a corolla tube. Margin: Entire. Orientation: Initially upright to eventually perpendicular to the peduncle. Texture, upper and lower surfaces: Smooth, glabrous; satiny. Number of ray florets per inflorescence: About 129 arranged in numerous whorls. Color: When opening, upper surface: Close to 9A overlain with close to 46A. When opening, lower surface: Close to 9B. Fully opened, upper surface: Close to 9A to 6A faintly overlain with close to 46A. Fully opened, lower surface: Close to 9B to 9C.

*Disc florets.*—Arrangement: Massed at center of receptacle. Length: About 5 mm. Diameter, apex: About 2 mm. Diameter, base: About 1 mm. Shape: Tubular; elongated. Apex: Five-pointed. Number of disc florets per inflorescence: About 35. Color: Immature: Close to 144A. Mature, apex: Close to 12A. Mature, mid-section and base: Close to 155D.

*Phyllaries.*—Quantity per inflorescence: About 24 arranged in two to three whorls. Length: About 9 mm. Width: About 4 mm. Shape: Lanceolate. Apex: Acute. Base: Truncate. Margin: Entire. Texture, upper surface: Waxy, smooth. Texture, lower surface: Pubescent. Color, upper surface: Close to 147A. Color, lower surface: Close to 146A.

*Peduncles.*—Length, terminal peduncle: About 3 cm. Length, fourth peduncle: About 5.9 cm. Diameter: About 2 mm. Strength: Strong. Texture: Pubescent. Angle: About 45° from vertical. Color: Close to 146A.

*Reproductive organs.*—Androecium: Present on disc florets only. Anther length: Less than 1 mm. Anther color: Close to 12A. Pollen amount: None observed. Gynoecium: Present on both ray and disc florets. Style length: About 5 mm. Style color: Close to 144A. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Dazzling Yonew York', as illustrated and described.

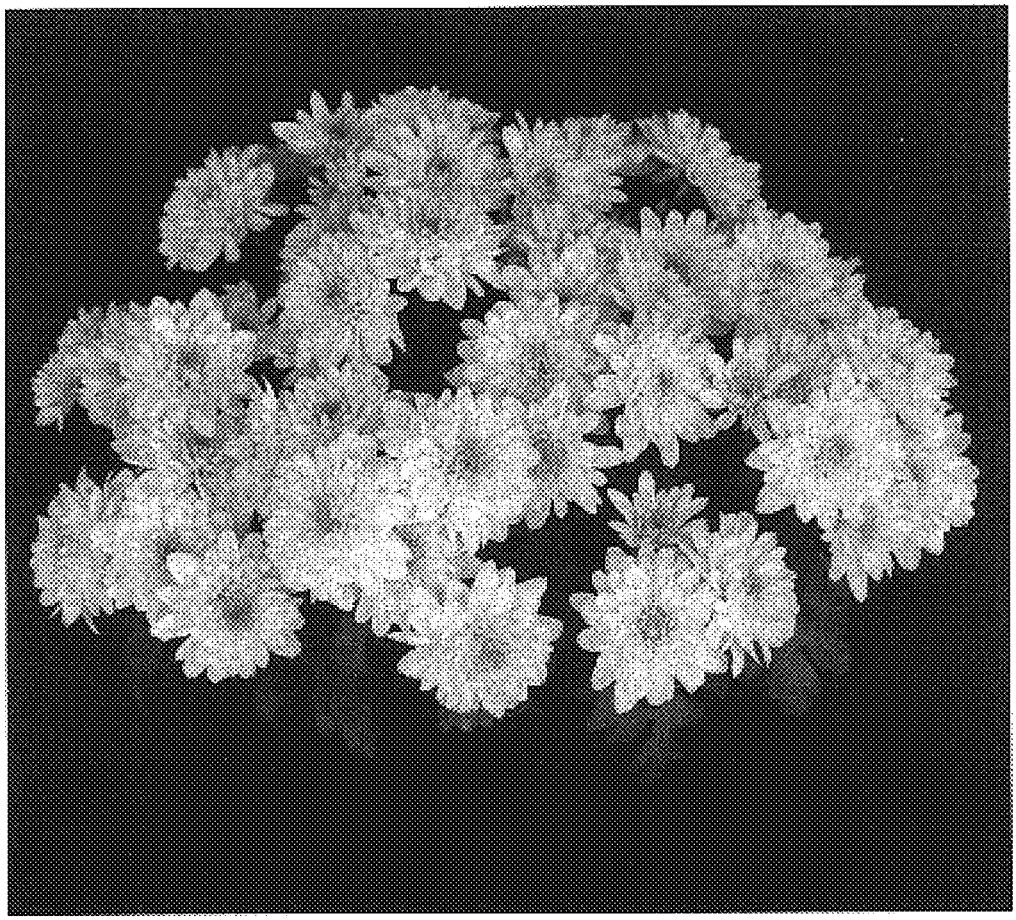

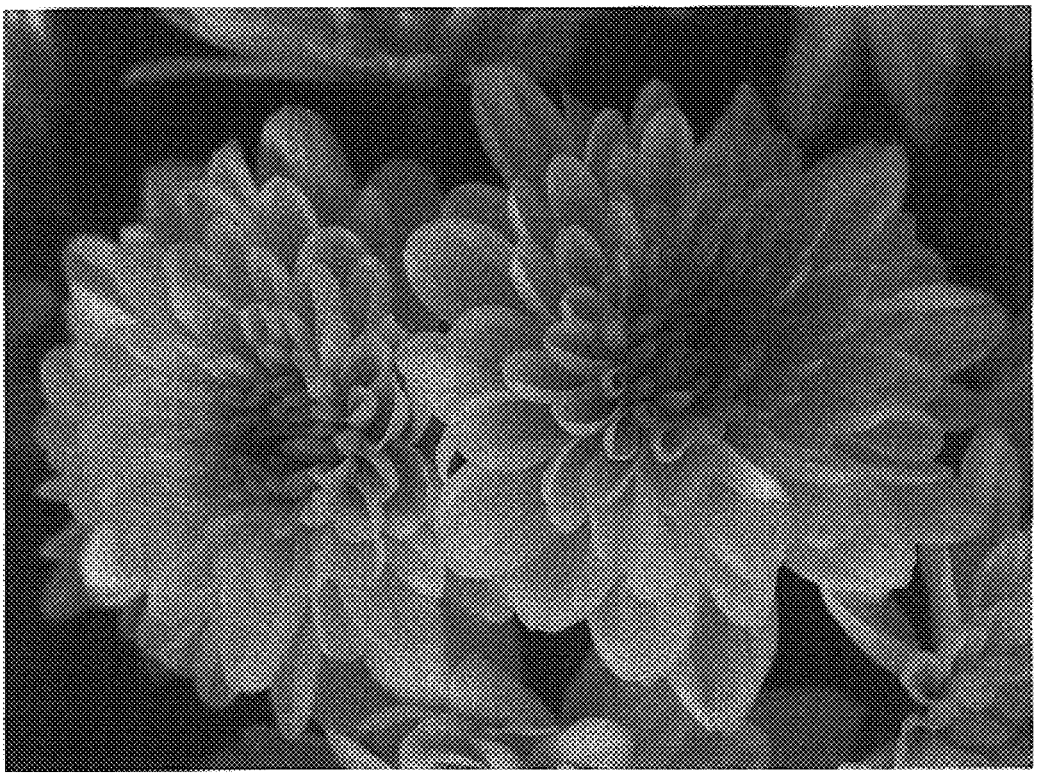

* * * * *